United States Patent [19]

Jimenez et al.

[11] 4,368,173

[45] Jan. 11, 1983

[54] REACTOR FOR OXICHLORINATION OF ETHYLENE AND PROCESS THEREFOR

[75] Inventors: Humberto D. Jimenez, Mexico City; Emilio W. Mora, Puebla, both of Mexico

[73] Assignee: Instituto Mexicano del Petroleo, Mexico

[21] Appl. No.: 186,159

[22] Filed: Sep. 11, 1980

[30] Foreign Application Priority Data

Sep. 12, 1979 [MX] Mexico .................................. 179250

[51] Int. Cl.³ ............................................... B01J 8/06
[52] U.S. Cl. .................................... 422/197; 422/202; 422/220
[58] Field of Search ............... 422/196, 197, 202, 220; 261/114 A

[56] References Cited

U.S. PATENT DOCUMENTS

| | | | |
|---|---|---|---|
| 2,198,555 | 4/1940 | Wilson et al. | 422/197 |
| 2,356,700 | 8/1944 | Rupp et al. | 422/202 |
| 3,198,727 | 8/1965 | Lifland | 422/197 X |
| 4,140,625 | 2/1979 | Jensen | 422/220 X |
| 4,192,835 | 3/1980 | Powers | 261/114 A |
| 4,233,269 | 11/1980 | Kaye et al. | 422/220 X |

OTHER PUBLICATIONS

*Hydro Carbon Processing;* Nov. 1975, pp. 214–217; "Vinyl Chloride".
*Hydro Carbon Processing;* Mar. 1979; pp. 75–88; "Vinyl Chloride Monomer."

*Primary Examiner*—Richard L. Chiesa
*Attorney, Agent, or Firm*—Finnegan, Henderson, Farabow, Garrett & Dunner

[57] ABSTRACT

The present invention refers to an improved reactor for oxichlorination of ethylene and to the process used therefor, which in a general way proceeds in accordance with the following reaction:

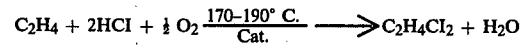

$$C_2H_4 + 2HCl + \tfrac{1}{2} O_2 \xrightarrow[\text{Cat.}]{170-190^\circ \text{ C.}} C_2H_4Cl_2 + H_2O$$

the catalyst being a fluidizable solid of Cu salts and oxides, the improvement being characterized in that the process is carried out in a multitubular reactor which comprises a gas distributing diffusor including a cap ferrule and granulated nickel.

7 Claims, 7 Drawing Figures

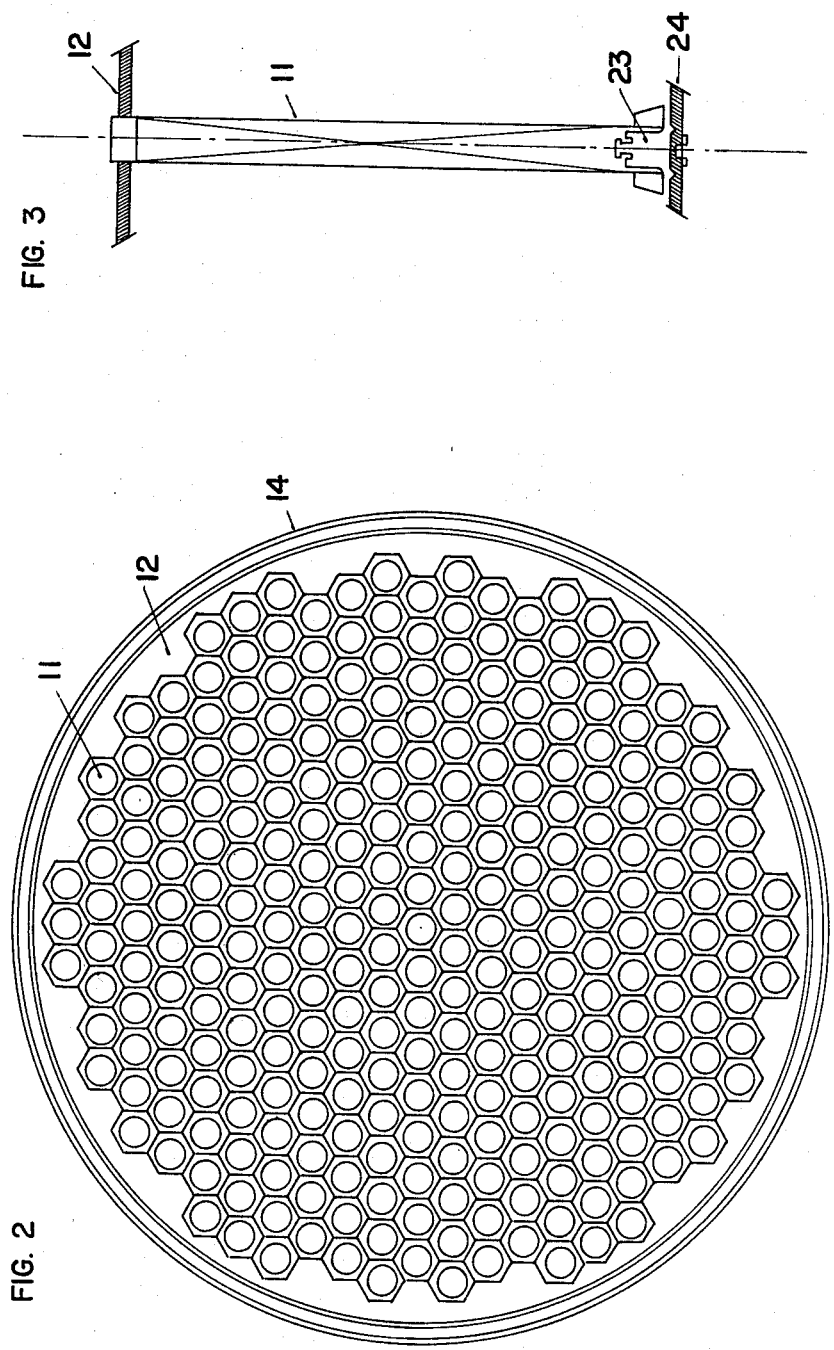

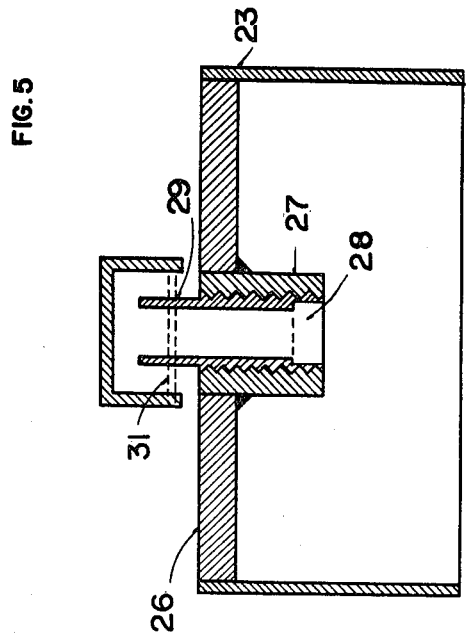
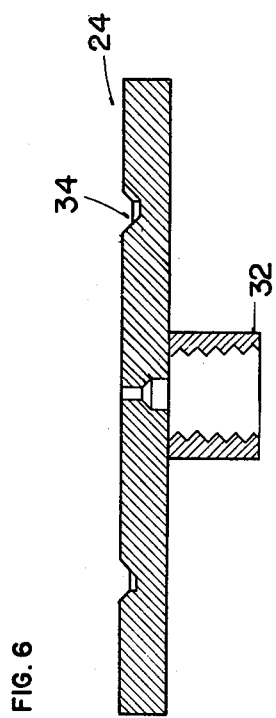
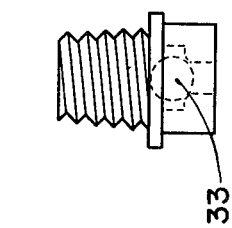

REACTOR FOR OXICHLORINATION OF ETHYLENE AND PROCESS THEREFOR

BACKGROUND OF THE INVENTION

The invention is related to an ethylene oxichlorination process in the presence of a catalyst the efficiency of which is remarkably improved by the use of an especially designed reactor which maintains a fluid catalytic bed in the reactor tubes by the use of a cap ferrule and a fixed bed of granulated nickel.

Most of the known processes for halogenation of aliphatic hydrocarbons and in particular to obtain 1,2 dichloro ethane are generally carried out through direct chlorination of ethylene or through oxichlorination of ethylene.

The direct chlorination of ethylene to produce 1,2-dichloro ethane is conducted in a liquid phase reactor by mixing intimately ethylene and chlorine in liquid dichloro ethane. In general, these reactions are conducted in the presence of catalysts such as ferric chloride.

Oxichlorination of ethylene to produce 1,2 dichloro ethane is also carried out in reactors, in the presence of fluid or fixed catalytic beds, under moderate temperatures and pressures. The catalysts used in this type of reaction are in most cases copper based, such as copper chlorides and sodium or potassium chloride, deposited on an adequate support. Other types of catalysts are also known which are constituted by rare earths metallic chlorides, sulphate salts and ferric chloride.

As for the operating conditions, it happens that at temperatures above 300° C. secondary reactions usually take place, deactivating the catalyst used when same undergoes a higher coking; the sublimation of copper is also undesirably increased. The by-products formed by secondary reactions during oxichlorination of ethylene are in general vinyl chloride, ethyl chloride, 1,1 dichloro ethane, trichloroethylene, methylene chloride, etc. These by-products are formed depending on the selected process and all of them cause problems in the obtainment of 1,2 dichloro ethane.

According to the prior art, there exist at the present time several processes to obtain chlorinated hydrocarbons, such as the processes of B. F. Goodrich, PPG Industries, Inc., Rhone-Poulenc, S.A., Monsanto Co., etc.

The Goodrich process produces dichloro ethane from ethylene, chlorine and air, through the stoichiometric reaction:

$$Cl_2 + C_2H_4 \rightarrow C_2H_4Cl_2$$

or by means of oxichlorination of:

$$C_2H_4 + 2HCl + \tfrac{1}{2}O_2 \rightarrow C_2H_4Cl_2 + H_2O$$

The latter reaction is conducted in a fluid bed of a copper chloride catalyst. The reaction is carried out in a specially designed reactor made of carbon steel.

The PPG Industries, Inc. process is conducted in a direct chlorination unit, combining chlorine and ethylene in a liquid phase in accordance with the reaction:

$$C_2H_4 + Cl_2 \rightarrow C_2H_4Cl_2$$

or in an ethylene oxichlorination unit in which oxygen and HCl are reacted in a vapor phase in the presence of a catalyst developed by PPG, in accordance with the reaction:

$$C_2H_4 + 2HCl + \tfrac{1}{2}O_2 \xrightarrow{Cat.} C_2H_4Cl_2 + H_2O$$

The raw dichloro ethane of both processes is combined with the recycled dichloro ethane in the pyrolysis unit and is purified by distillation.

The Rhone-Poulenc, S.A. process produces dichloro ethane either by direct chlorination where chlorine is reacted with ethylene in liquid dichloro ethane in accordance with the reaction:

$$C_2H_4 + Cl_2 \rightarrow C_2H_4Cl_2$$

or through oxichlorination of ethylene in accordance with the reaction:

$$C_2H_4 2HCl + \tfrac{1}{2}O_2 \rightarrow C_2H_4Cl_2 + H_2O$$

The oxichlorination process is a vapor phase reaction which is conducted in a carbon steel reactor that operates under moderate pressures.

In the direct chlorination process, the ethylene and chlorine gases are loaded into the reactor which contains liquid dichloro ethane as a reaction medium and cooling system, and the dichloro ethane which is produced is treated thereafter to withdraw the chlorine and HCl content. The raw dichloro ethane is purified by distillation.

Other known techniques such as the Stauffer process produce dichloro ethane either by direct chlorination of ethylene where ethylene and chlorine are reacted in a liquid phase and under controlled reaction conditions, the obtained product is combined with the oxichlorination product, and then it is washed and distilled, or the dichloro ethane is obtained by the combination of the oxi reaction with the HCl recycle, fresh ethylene and air in a fixed catalytic tubular reactor, or else by the modified process of oxichlorination of ethylene based on oxygen, where the condensed dichloro ethane is compressed and recirculated to the first oxi reactor, using an excess of ethylene to increase the HCl conversion and to decrease the formation of by-products.

Among other technologies which are known for the obtainment of dichloro ethane, there are the MTC Chemical Technology process, and the Toyo Soda Technology.

The MTC technology uses a boiling liquid process for the direct chlorination reaction where the reaction heat is dissipated with an outgoing stream of gaseous dichloro ethane which is externally condensed and sent to purification.

The MTC technology also uses the oxichlorination process, and it is characterized by the use of oxygen batches and a fluidized bed reactor, the effluent gases from the reactor being cooled rapidly with circulating dichloro ethane followed by a caustic neutralization.

The Toyo Soda process is similar to the one developed by the Stauffer technology, its main differences being the use of an absorber-separator on the gas effluent of vent oxi and the dehydration of the raw dichloro ethane before the purification.

Monsanto Technology—This process is similar to the Stauffer technology, and it is based on recirculating the HCl produced in the vinyl chloride plant to an oxichlorination reactor. The process may be carried out in the same manner as those mentioned before, that is by direct chlorination or by oxichlorination.

The Monsanto oxichlorination process is a vapor phase reaction and it is carried out in a carbon steel reactor which operates at moderate pressures, in the presence of a fluid bed catalyst.

The efficiency of processes that are carried out in reactors varies depending on the design of the chosen reactor. Reactors may be fixed bed catalytic reactors or fluidized bed catalytic reactors; in general, it has been observed that the fluidized bed reactors provide a better ethylene conversion (94-97%), of HCl (95-97%), and a better selectivity of 1,2 dichloro ethane (94-96%), than the fixed bed reactors. These efficiency results are also subject to the type of reactor design used and to the quality of the raw materials employed.

The fluidized bed oxichlorination reactors generally comprise diffusing elements for the reaction gases made of porous plates which perform an adequate distribution of the gases, such porous plates being commonly known as ferrules and constituted by a porous plate with a filtering element.

The known reactors that operate with this type of ferrules present some disadvantages in their use due to the fact that the porous plate is only useful for clean feed gases, from the known experiences in plants of chlorinated derivatives it is observed that the stream of anhydrous HCl which results from the pyrolysis of 1,2 dichloro ethane is not completely clean in spite of its filtration before its use; this causes in a period of 3 to 4 months of use of the porous plate ferrule a plugging of the filter as well as of the porous plate.

The plugging of the porous plate and the temperature difference between the operating temperature of approximately 180° C. and the subsequent cooling of the reactors are factors that cause the premature breakage of the porous plate.

The plugging of the porous plate also causes a decrease of the fluidification speed which results in the compression of the catalyst in the reactor tubes; this phenomenon causes the increase in the formation of secondary reactions which affect the efficiency of the process.

The applicant has developed a process to obtain 1,2 dichloro ethane which is more efficient, by the oxichlorination of ethylene in a tubular reactor which comprises a gas diffusor that is especially designed with a cap ferrule which is improved by the incorporation of a nickel granule bed that constantly maintans a fluid catalyst during the reaction. Under these conditions, it is not necessary to make a previous purification of the raw materials, particularly of the HCl stream.

There being no plugging of the ferrule, the formation of secondary reactions created by the compression of the catalyst is avoided, and consequently the efficiency of the process is considerably increased.

BRIEF SUMMARY OF THE INVENTION

The invention refers to an improved oxichlorination reactor and to a process to obtain 1,2 dichloro ethane by the oxichlorination of ethylene in the presence of a fluid catalyst bed, the reaction being carried out in a specially designed carbon steel tubular reactor which comprises a diffusor for the distribution of gases constituted by a cap ferrule and nickel granules that permit conducting the reaction at moderate temperatures and pressures.

It is, therefore, an object of the present invention to provide a tubular reactor that is especially designed with a gas diffusor which is composed by the combination of a cap ferrule and a nickel granule bed.

Another object of the invention is to provide a reactor in which the process is carried out without the compression of the catalyst in the reactor tubes, by which the formation of increased heating areas in the reactor is avoided, which results in a less efficient process due to the formation of secondary reactions.

Still another object of the present invention is to provide a gas diffusor combined with a nickel granule bed which maintains constantly an adequate fluidification of the gases while the catalytic activity of the catalyst lasts.

A further object of the present invention is to provide a more efficient process to obtain 1,2 dichloro ethane by the oxichlorination of ethylene which maintains a catalytic bed that is always in a fluidized condition.

Another object of the present invention is to provide a more efficient process to obtain 1,2 dichloro ethane while avoiding the formation of secondary reactions.

BRIEF DESCRIPTION OF THE DRAWINGS

The drawings that describe the reactor are presented with the purpose of a better illustration of the invention.

FIG. 2 is an elevated view of the lower mirror of the reactor calender. In this view the ferrule holder coupled to the calender tubes is observed, fixed by stud bolts.

FIG. 3 is a longitudinal vertical section of one of the tubes of the calender of FIG. 2.

FIG. 5 is a vertical section of the ferrule of FIG. 4, in which the ferrule cap can be seen in more detail.

FIG. 6 is a longitudinal cross-section of the ferrule holder.

FIG. 7 is a cross-section of the check valve coupled to the ferrule holder of FIG. 6.

DETAILED DESCRIPTION OF THE INVENTION

Figure 1:
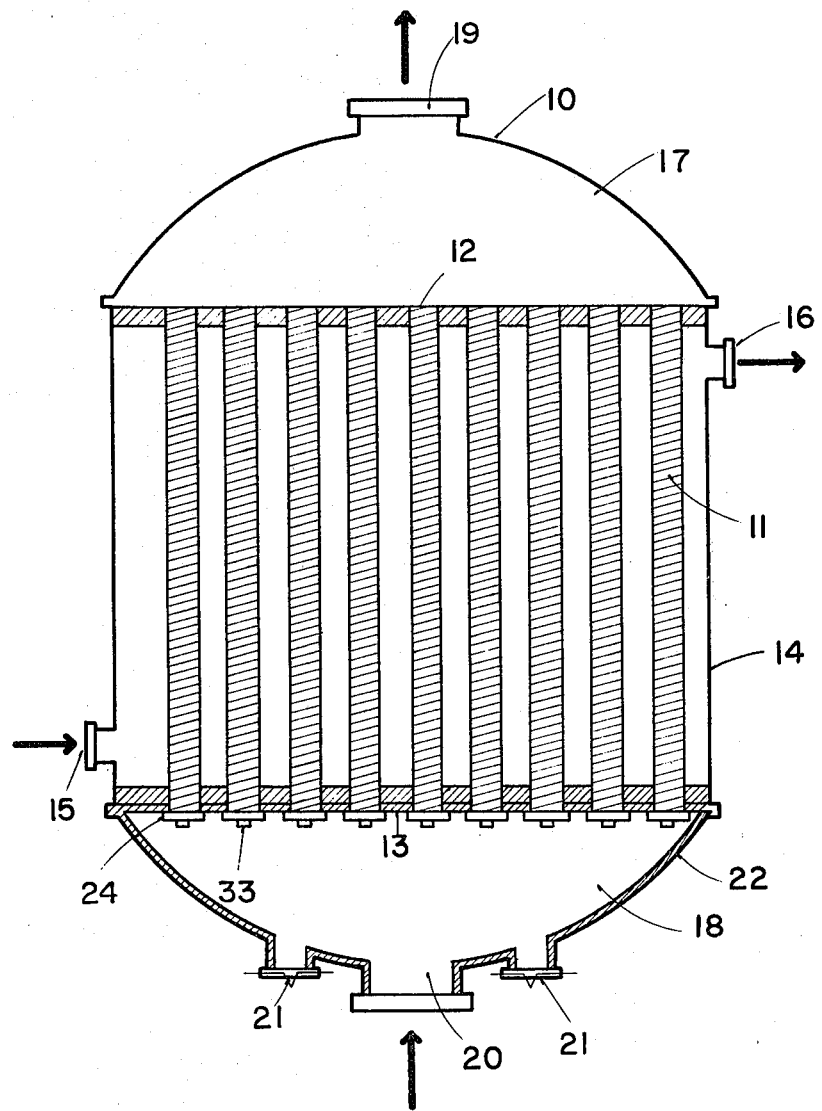
FIG. 1 is a longitudinal section of a vertical view of the carbon steel reactor in which the oxichlorination reaction is carried out for the obtainment of 1,2 dichloro ethane. In this section the vertical heat exchange type tubes can be observed where the fluid catalyst is located.

The process of the present invention is carried out by oxichlorination of ethylene with anhydrous hydrochloric acid and oxygen in the presence of a fluid catalyst bed to obtain 1,2 dichloro ethane in accordance with the reaction:

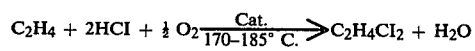

The reaction is carried out in a catalytic multitubular type reactor which maintains a fluid catalyst bed by means of the special design of a cap ferrule combined with a nickel granule bed of from 35 to 12 mesh size which in turn functions as distributor of the reaction gases in each of the reactor tubes.

The oxichlorination reaction of ethylene is exothermic and the generated heat is used to produce saturated vapor, approximately 10.5 kg/cm² in the reactor casing, the generated vapor being used in some of the process operations. The operating temperatures in the fluidized bed zone may be between 190° and 240° C.

The catalyst used when in repose is a solid based on a mixture of copper salts and oxides or else of copper salts such as Cu chlorides supported by alumina. The catalyst deposited on the nickel granule bed inside the reactor tubes changes its state of repose to the fluid state due to the passing of gases through the ferrule and through the spaces that are free between the granulated spheres.

The HCl used in the reaction of oxichlorination originates in an HCl stream which is formed during the pyrolysis of dry 1,2 dichloro ethane in the obtainment of vinyl chloride.

The theoretical molar relation of ethylene/anhydrous HCl/oxygen is 1/2/0.5.

In accordance with the different molar relations of the hydrochloric acid/Ethylene-Air loads and the feeding speeds, it is observed that the most advisable stoichiometrical molar reaction is:

Ethylene/Anhy HCl/Oxygen=1/1.7/0.57 since the conversion is practically constant at fluilizing speeds of 0.14 to 0.20 m/sec.

The variations outside the relation of Ethylene/HCl/Oxygen=1/1.7/0.57 involve the formations of secondary reactions such as the formation of trichloro ethane according to the reaction:

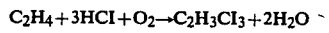
$C_2H_4 + 3HCl + O_2 \rightarrow C_2H_3Cl_3 + 2H_2O$

Once the reaction is carried out, the raw gaseous 1,2 dichloro ethane formed mainly by 1,2 dichloro ethane, $CO_2$, CO and HCl is raidly cooled to approximately 90° C. in an HCl washer to condense part of the 1,2 dichloro ethane and to eliminate the HCl; the gaseous product is thereafter sent to a neutralization tower with NaOH, where carbonates are formed and most of the 1,2 dichloro ethane is condensed. The mixture formed thereby is sent to a separation tank where the 1,2 dichloro ethane is separated.

In the following examples the different operating conditions and process modes of oxichlorination of ethylene are illustrated, where said process is conducted in a reactor of a cap ferrule type. Information is also provided about the operating conditions of a reactor in which a porous plate ferrule is employed.

EXAMPLE NO. 1

Into a multitubular reactor of a cap ferrule and nickel granule at a temperature of about 120° C., a stream of 17 to 18% mole of ethylene, 30 to 31% mole of anhydrous HCl, and 10 to 11% mole of $O_2$ is fed, the remainder being $N_2$, and the reaction being carried out at an approximate pressure of 2 kg/cm$^2$, in the presence of a fluid bed of a catalyst made of copper chloride or copper oxichloride with an alumina support of 60 to 100 mesh size; and a fine bed of nickel granules of from 3 to 12 mesh size. The reaction is conducted at temperatures comprised in the range of 190° to 240° C., with a relation of feed to the reactor of ethylene/hydrochloric acid/oxygen molar proportions of approximately 1/1.7/0.57.

The outcoming gases from the reactor are condensed in a washing tower of HCl with a fast cooling to approximately 90° C., where HCl is eliminated without reacting. Thereafter, the raw 1,2 dichloro ethane constituted by 1,2 dichloro ethane, CO and $CO_2$ is sent to a neutralization tower with 4% soda; in later stage the 1,2 dichloro ethane is stripped and the 1,2 dichloro ethane is sent to a storage tank where a purity of 98.5% of dichloro ethane is determined.

An evaluation of the routine day-to-day analyses of the process is carried out during the first days of initiation of the process, and it is determined that the optimum conversion of HCl is 99.4%, and that is practically constant at fluid speeds of from 0.137 to 0.22 m/sec. The selectivity is of 98.9%.

After an operation time of three months, a new evaluation of the routine analyses of the outcoming gases from the reactor is carried out which shows the following values:

HCl conversion %: 97
Selectivity, %: 98.9
Outgoing temperature: 210° C.

The above results indicate that the catalyst used has maintained its fluidity without compression thereof in the reactor tubes, in view of which the plugging problem in this ferrule does not exist, since it continues maintaining a good process efficiency.

EXAMPLE NO. 2

In accordance with the process of Example 1, a reactor with a temperature of about 120° C. and a pressure of 2.05 kg/cm$^2$ g is fed with a stream of 28% mole of HCl, 19.5% mole of ethylene, 11.02 of $O_2$, and the remainder of $N_2$. The catalytic reaction is conducted at a temperature comprised between the range of 220°-230° C. and a flow speed of 0.17 to 0.18 m/sec.

An evaluation of the routine analyses is made after a period of three months and 15 days of the outcoming gases from the reactor, which shows the following results:

% of HCl conversion: 99.92
Selectivity, %: 98.8
Outcoming temperature: 210° C.

The above results indicate that the catalyst used has maintained its fluidity without compression thereof in the reactor tubes, in view of which the plugging problem in this ferrule does not exist, since it continues to maintain a good process efficiency.

EXAMPLE NO. 3

In accordance with the process of Example 1, a reactor with a temperature of about 120° C. is fed with a feed mixture which comprises from 18.5 to 18.7% mole of ethylene, from 30.4 to 30.6% mole of anhydrous HCl and from 10.4 to 10.7% mole of $O_2$, the remainder being $N_2$, the feeding speed being between 0.17 and 0.18 m/sec.; the catalytic reaction being conducted at temperatures comprised in the range of 190°-240° C., and at pressures of from 1.9 to 2 kg/cm$^2$.

An evaluation of the routine analyses of the outcoming gases from the reactor is conducted after a period of 4 months counted from the initiation of the process, which shows the following results:

HCl conversion %: 99.57
Selectivity, %: 98.8
Outgoing temperature: 210° C.

EXAMPLE NO. 4

In accordance with the process of Example 1, a multitubular ferrule and nickel granule type of reactor at an approximate temperature of 120° C. is fed with a feed mixture which comprises 20.75% mole of ethylene, 25.88% mole of anhydrous HCl and 11.11% mole of O$_2$, the remainder being N$_2$, the feeding speed being 0.18 m/sec., the catalytic reaction being carried out at temperatures comprised in the range of 230°–240° C., and at pressures of 2.25 to 2.30 kg/cm$^2$.

An evaluation of the routine analyses carried out daily with the outgoing reactor gases is made after a period of 4 months after the date of initiation of the process, which shows the following results:

HCl conversion percentage: 97.4
Selectivity, %: 98.7
Outgoing temperature: 210° C.

EXAMPLE NO. 5

A fluidized bed porous plate ferrule reactor type of synterized Inconel is fed with a mixture which comprises ethylene, hydrochloric acid and oxygen in a molar relation of approximately 1/1.70/0.57 with an excess of ethylene to maximize the HCl conversion and the selectivity of 1,2 dichloro ethane, the reaction being carried out at a temperature of approximately 200° to 250° C. and at a pressure of 2 atmospheres of abs, in the presence of a copper chloride catalyst supported on alumina.

The gases from 1,2 dichloro ethane in a raw form are sent to an HCl washer and immediately thereafter they are treated with caustic soda, the product being dryed and sent to a direct chlorination reactor to react the residual ethylene and to recover the 1,2 dichloro ethane.

An evaluation of the routine analyses is made after the first 5 days of the process initiation, of the outcoming gases of the reactor, and the following results are determined:

HCl conversion %: 80.0
Selectivity, %: 81.0
Outcoming temperature °C.: 220

The obtained results which indicate a low selectivity and a low conversion are probably due to the fact that the porous plate has been plugged, as well as the ferrule holder filters. The fluidification speed is lower than the limit (Approx. 0.122 m/sec.) due to the catalyst compression in the reactor tubes.

DESCRIPTION OF THE EQUIPMENT AND PROCESS IN ACCORDANCE WITH THE DRAWINGS

Figure 4:
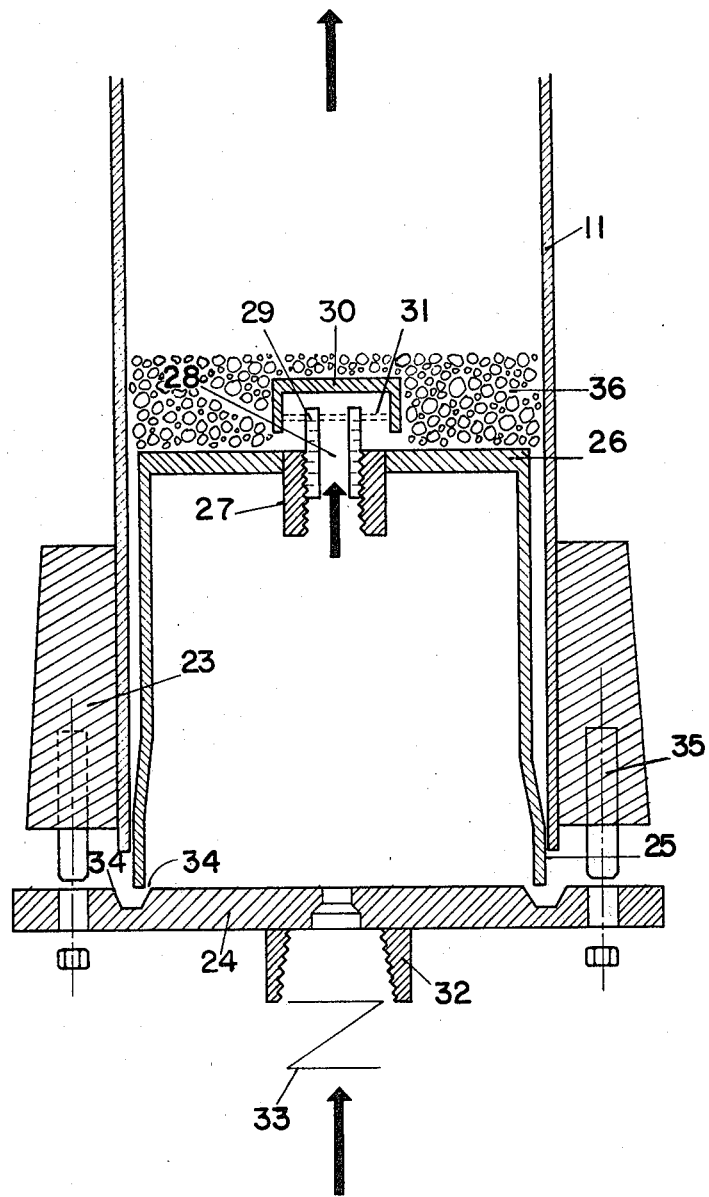
FIG. 4 is a vertical section of the lower portion of the tube of FIGS. 2 and 3, in which the ferrule, the ferrule holder and the nickel granule bed can be observed in more detail.

The equipment or apparatus which is the object of the invention, in accordance with FIGS. 1 through 7, is a carbon steel tubular reactor 10 of the heat exchange type, basically constituted by a vertical tube calender 11 which are joined together by an upper mirror 12 and a lower mirror 13, the free spaces between the tubes forming together a reactor casing 14 which has a water feed 15 as a dissipating means of the reaction heat in the lower end of a vapor outlet 16 which is generated during the oxichlorination reaction on the opposite upper end.

The casing 14 is attached on its upper portion to a dome 17 which functions as an upper degasifying portion and in its lower portion is joined to a lower header 18 which operates as a distributing chamber for the reactants feed. On the upper end of dome 17 is located the outlet 19 for the reaction gases, while on header 18, on its upper middle portion, is located the inlet 20 for feeding of reactants HCl, Ethylene and Air; on the sides of feeding 20 are located the rupture discs 21 which function as protection elements when an overpressure risk or limit of explosive mixtures exist.

Due to corrosion of the reactants, header 18 is coated with a stainless steel material 22. On the inside of each of tubes 11 of the calender and on the side of a mirror located in the lower portion 13, there is a cap ferrule 23 supported by a ferrule holder 24. Cap ferrule 23 is a diffusing element of the reaction gases which comprises a sleeve 25 made of stainless material, which is concentrically rolled to the inside of tube 11, the upper end of said sleeve 25 being welded to a plate 26 which functions as a cap ferrule that acts as a cap bubbler 27 which in turn presents a vertical orifice 28 for the admission of gases, the threaded inside of which permits the coupling of a protuberant conduit 29 to hold the cap 30 with the bubbler 27 by means of pins 31.

The ferrule holder 24 is a metallic hexagonal plate which functions as a ferrule support and presents in its center a tubular protuberance 32 threaded on its inside portion which couples a check valve 33 which has the function to act when there exists a back flow in the inside of reactor 10. Ferrule holder 24 has a concentric recess 34 on sleeve 25 in which a packing 34 which permits to seal hermetically the ferrule against the ferrule holder 24 by means of the tightening of the stud bolts fixed coaaxially to tube 11.

On the upper portion of ferrule 23, that is, on plate 26 is located a nickel granule bed; these spheres are distributed covering all the surface of plate 26 and they overflow the height of the cap bubbler 27; granule bed 36 has the function of making the gas diffusion distributed by cap ferrule 23 more effective.

| TYPICAL WORKING CONDITIONS OF THE REACTOR | |
|---|---|
| Pressures of: | Operation |
| Inlet | 1.85 |
| Outlet | 0.9 |
| P | 0.95 |
| Temperatures of: | Operation |
| Inlet | 120° C. |
| Outlet | 210° C. |
| Beds | 180–235° C. |
| Stoichiometric Relations: (Reactor Inlet) Ethylene/HCl/oxygen 1/2/0.5 | |
| Operating Relations: | |
| (Inlet) $\frac{HCl}{Ethylene} = 1.7$ | |
| $\frac{Oxygen}{HCl} = 0.355$ | |
| Reactor Outlet: HCl 0.44% mole Conversion % 99.92 | |

TEST WITH A SINTERIZED INCONEL POROUS PLATE FERRULE

A natural gas pressure is applied in the feeding header of 2.5 kg/cm$^2$, an equivalent natural gas flow of 0.7 feet/sec. (34% of rotameter of 22.8 m$^3$/h) with conditions: air at 20° C. and 2 kg/cm$^2$.

It is observed that fluidification is good and the distribution of catalyst is also good, after which 10 g of lampblack were added to the feeding header which was brought into operation to arrive to a pressure of 2.5 kg/cm$^2$ g; after a short period it is observed that there is a plugging in the porous plate and thereafter a breakage of same.

TEST TO DEMONSTRATE THE EFFICIENCY OF THE CAP FERRULE-NICKEL GRANULE

A natural gas pressure is applied to the header that is used for feeding the reactor at 2.5 kg/cm$^2$ g with a natural gas flow of the equivalent of 0.7 ft/sec. (34% of rotameter of 22.8 cm m/hr. with conditions at 20° C. in air and 2 kg/cm$^2$ g).

It is observed that fluidification and distribution of air are good, and 10 g of lampsmoke were added to the feeding header and the operation of same was started until reaching a pressure of 1.6 kg/cm$^2$, no plugging or channeling being observed in the ferrule.

We claim:

1. An improved multitubular heat exchanger type reactor to carry out the oxichlorination of ethylene to obtain preferably 1,2 dichloro ethane comprising:
   a calender reactor including a casing and a system of vertical tubes;
   a first mirror joined to the upper ends of the vertical tubes;
   a second mirror joined to the lower ends of the vertical tubes;
   a degasifying chamber formed as an upper dome attached to the upper portion of the casing;
   a distributing chamber for the reactants, said chamber being formed as a lower dome or feeding header attached to the lower portion of the casing;
   at least one diffusing element for the reaction gases individually coupled to the inside of at least one reaction tube, wherein each said diffusing element comprises a ferrule including a metallic cylindrical ferrule sleeve, a horizontal annular stainless metallic plate attached to the upper edge of said cylindrical sleeve, a tubular element affixed to the circular inner surface of said annular plate, a movable tubular element adjustably mounted inside said tubular element, and a ferrule cap mounted on said tubular element;
   a holder for said ferrule attached to the lower end of the calender tubes; and
   a metallic granule catalyst bed located on the cylindrical plate of the ferrule.

2. An improved multitubular reactor in accordance with claim 1, wherein the metallic granule bed covers and overtops the cap height, in order to increase the distribution area of the gases and to improve the catalyst fluidity.

3. An improved multitubular reactor in accordance with claim 1, characterized in that the ferrule holder is a metallic hexagonal plate which presents on its center a conduit to which is coupled a one-way valve which controls any backflow inside the reactor.

4. An improved multitubular reactor in accordance with claim 1, wherein the ferrule holder includes on its upper surface a recess for receiving the ferrule sleeve and packing in said recess for sealing the ferrule joint between the ferrule holder and the sleeve.

5. An improved multitubular reactor in accordance with any one of claims 1, 2, 3, or 4, characterized in that the ferrule holder comprises fastening elements for attachment to the ferrule cap.

6. An improved multitubular reactor in accordance with claim 1, characterized in that the calender casing presents on its lower end a water feed to dissipate the reaction heat, and on its upper end an outlet for vapor generated during the reaction.

7. An improved multitubular reactor in accordance with claim 1, characterized in that on the sides of the feed inlet of the reactor header there are located two rupture discs which function as safety elements when there exists an over-pressure above the working pressure of the reactor.

* * * * *